(12) United States Patent
Morris et al.

(10) Patent No.: US 8,754,574 B2
(45) Date of Patent: Jun. 17, 2014

(54) MODULAR ARRAY AND CIRCUITS FOR ULTRASOUND TRANSDUCERS

(75) Inventors: Richard Lee Morris, Maple Valley, WA (US); David A. Petersen, Fall City, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 361 days.

(21) Appl. No.: 13/090,941

(22) Filed: Apr. 20, 2011

(65) Prior Publication Data

US 2012/0267981 A1 Oct. 25, 2012

(51) Int. Cl.
*B06B 1/06* (2006.01)
(52) U.S. Cl.
USPC .......................................... 310/334; 310/348
(58) Field of Classification Search
USPC ........... 310/322, 334, 335, 365, 366; 600/459
See application file for complete search history.

(56) References Cited

U.S. PATENT DOCUMENTS

| 6,014,898 | A  | * | 1/2000  | Finsterwald et al. ............ 73/642 |
| 7,304,415 | B2 |   | 12/2007 | Petersen et al. |
| 7,557,489 | B2 |   | 7/2009  | Petersen et al. |
| 2004/0100163 | A1 | * | 5/2004 | Baumgartner et al. ....... 310/334 |
| 2009/0015101 | A1 | * | 1/2009 | Petersen et al. ............... 310/327 |

* cited by examiner

*Primary Examiner* — Derek Rosenau (57) ABSTRACT

Modular electronics are provided for a multi-dimensional array. The electronics are positioned perpendicular to the array in modules. The modules include frames to support the electronics and provide for electrical connection between the array and the electronics. The frames include thermally conductive material to transfer heat away from the electronics and the array. The frames form a surface to support part of the array and a single layer of flexible circuit material with pads and traces over the surface for electrical connection. The flexible circuit material allows connection to the electronics at a pitch different than the pitch of the array. The modules allow the same electronics parts to be used with different sized arrays. The traces and pads of the flexible circuit material may be changed for different arrays without having to redesign the electronics and/or modules.

12 Claims, 3 Drawing Sheets

MODULAR ARRAY AND CIRCUITS FOR ULTRASOUND TRANSDUCERS

BACKGROUND

The present embodiments relate to ultrasound transducers. In particular, modular ultrasound transducers are provided.

Matrix or two-dimensional ultrasound transducers require complex electronics to manage the large number of elements and to reduce the resulting signal count to a manageable number. For example, sub-array beamforming partially beamforms data from different sub-apertures together, reducing the number of channels to a number of imaging system beamformer channels.

To limit the number of cables, the partial beamforming circuits are positioned in the ultrasound probe housing. However, the circuits may not be close enough to the elements. The small elements have a high impedance. This high impedance may require ultra-short connections to the electronics in order to maximize sensitivity and dynamic range. Conversely, the size requirements for the partial beamforming circuits may require longer connections.

BRIEF SUMMARY

By way of introduction, the preferred embodiments described below include methods, transducer probes, and systems for modular electronics for a multi-dimensional array. The electronics are positioned perpendicular to the array in modules. The modules also include frames to support the electronics and allow for electrical connection between the array and the electronics. The frames may include thermally conductive material (e.g., metal) to transfer heat away from the electronics and the array. The frames may form a surface to support part of the array and a single layer or two layers of flexible circuit material with pads and traces over the surface for electrical connection. The flexible circuit material allows connection to the electronics at a pitch different than the pitch of the array. Any one or more of these features may be used in a given transducer probe.

By using multiple modules, a transducer probe matched to the size of the array may be provided. The modules allow the same electronics parts to be used with different sized arrays. The traces and pads of the flexible circuit material may be changed for different arrays without having to redesign the electronics.

In a first aspect, a transducer probe includes a multi-dimensional array of ultrasound transducer elements. A plurality of frames is stacked adjacent to the multi-dimensional array. Each of the frames includes metal structure extending from adjacent to the multi-dimensional array to a location spaced away from the multi-dimensional array. A plurality of circuits connects with the transducer elements. The plurality of circuits connects with respective frames where the location is further away from the multi-dimensional array than the circuits.

In a second aspect, a transducer probe includes a multi-dimensional array of ultrasound transducer elements. The ultrasound transducer elements are distributed in azimuth and elevation. A plurality of frames is positioned adjacent to each other such that a surface formed from the frames supports the entire multi-dimensional array. The frames each extend substantially perpendicularly from the multi-dimensional array and away from the surface. A plurality of circuits connects with respective frames such that the circuits are perpendicular to the multi-dimensional array. Flexible circuit material for each frame extends from the circuit or circuits and over the surface between the multi-dimensional array and the frames. Traces of the flexible circuit material over the surface connect with the ultrasound transducer elements.

In a third aspect, a method is provided for stacking an ultrasound probe. For each of a plurality of frames, one or more application specific integrated circuits are connected. For each of the frames, traces on flexible material connect to the circuits. The frames are stacked adjacent to each other. A multi-dimensional transducer array is placed on the stack of frames such that the circuits are substantially perpendicular to the multi-dimensional transducer array. The traces are electrically connected to the multi-dimensional transducer array such that a first two-dimensional pitch of the traces connected to the circuits is different than a second two-dimensional pitch of the traces electrically connected to the multi-dimensional transducer array.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A transducer construction may simultaneously increase the available electronic circuit area and minimizes the interconnection length. Modular electronic frames hold integrated or other circuits (e.g., application specific integrated circuits (ASICs)) at generally right angles to the acoustic array and provide a thermal conduction path. Thermal conduction through the structural alignment frames removes heat from the modular ASIC assembly. The generally perpendicular orientation for the ASIC may increase the usable ASIC space in the probe.

Inexpensive flex circuits are used to make chip-to-array interconnections. A single flex circuit wraps around the frame to connect one or more ASICs to the acoustic array. The flex circuits may be short while not constraining the array and chips to have matching pitches in either azimuth or elevation. One chip design may be reused for multiple types or sizes of arrays. The modular electronic assemblies may provide flexible pitch in both azimuth and elevation using a single ASIC design. Different flex circuits that either fan in or out to the desired pitch in azimuth or elevation are used with the same ASIC design. For example, the flex circuit only fans in or out in one dimension. Changing pitch in the other dimension is done on the element surface of the frame by adjusting the width of the frame and the pitch of the connections. The frames may vary in size or shape to stack modules to achieve the desired pitch in elevation or azimuth.

In alternative embodiments, an ASIC is embedded in a molding compound with a frame to form the module. Interconnections to the acoustic array are provided by embedded wires bonded to the ASIC.

Different frames may be used for different types of arrays. For example, rectangular frames establish a flat surface for flat transducers, and tapered frames establish a concave or convex surface for curved transducers.

The ASICs are bonded to frames. The frame structure may protect delicate ASIC devices.

Figure 1:
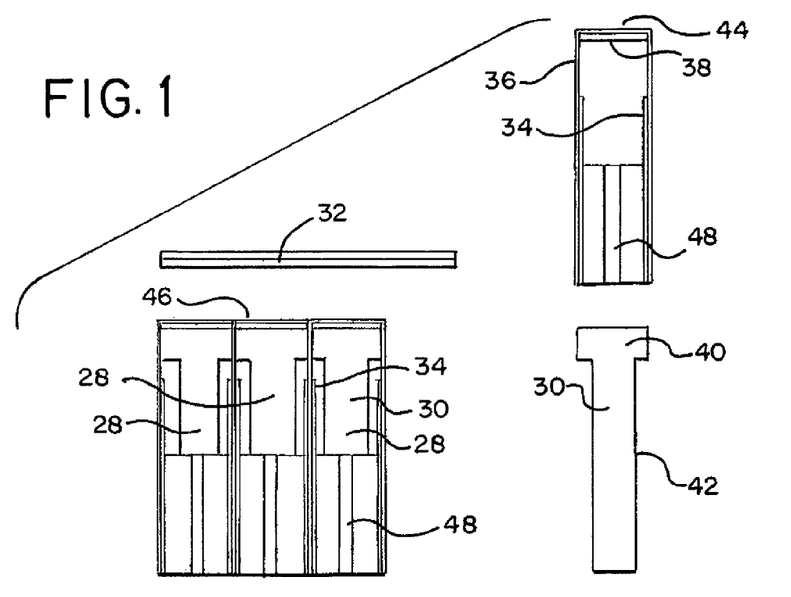
FIG. 1 is a cross-sectional view of a plurality of transducer modules according to one embodiment with an exploded view of one of the modules.

FIG. 1 shows a cross-section view of a modular ultrasound transducer probe with an exploded view of a module. The transducer probe is used as a transesophageal (TEE) probe, such as a two-dimensional array for scanning from within a patient's esophogeous. The ultrasound transducer probe may be used as an adult or pediatric cardiology transducer. A high element count gastro-intestinal (GI) transducer may be provided, such as a curved abdominal matrix (multi-dimensional) transducer array. Using modules with the same circuits but with or without changes in trace pitch for array connection allow scaling without circuit redesign to a variety of channel counts.

In the transducer probe shown in FIG. 1, a plurality of modules 28 is provided to support a multi-dimensional transducer array 32. Additional, different or fewer components may be provided. For example, matching layers, a lens, a probe housing, and/or cable are provided.

The multi-dimensional array 32 is a layer of transducer material. The layer of transducer material is a solid piezoelectric ceramic, composite, or other transduction material. Alternatively, the layer is a semiconductor with microelectromechanical devices for transduction, such as a plurality of drums or membranes and associated electrodes (e.g., capacitive membrane ultrasound transducer (CMUT)). The layer may include electrodes and/or matching layers. A grounding plane may be included above or below any matching layers for grounding the top side of the elements. The transducer layer may include multi-layer elements, such as two or three layers of piezoelectric with corresponding electrodes.

The transducer material is diced or formed into a plurality of elements. In one embodiment, the layer is bonded to the modules 28, and then elements are formed by dicing. Sub-elements may also be formed. In other embodiments, the elements are formed prior to bonding to the modules 28. The elements and corresponding kerfs align with the element contacts on the modules 28 for bonding.

The elements are spaced in a two, 1.25D, 1.5D, 1.75D, or other multi-dimensional array of elements. For a multi-dimensional array of elements (matrix array), the elements are spaced in a rectangular grid in elevation and azimuth. Each element is a cube or other volume shape. The elements are distributed over different dimensions, such as being N×M where both N and M are greater than one. Other grids may be used, such as hexagonal or triangular. Alternatively, the elements are spaced in a one dimensional pattern, such as being a single row of elements along a line or curve.

Each element includes electrodes on opposite faces or parts of the element. One electrode is positioned between the transducer material and the corresponding module 28. The other electrode is on the side of the element where acoustic signals are transmitted and received from the patient (e.g., the face of the transducer). The electrodes are deposited on the elements, formed by conductors on flex material (e.g., grounding plane on the side of the element for transmitting and receiving), or formed by wires, conductive surfaces, or other conductor of the modules 28. The electrodes adjacent the modules 28 are electrically isolated from each other, such as by dicing into a pattern matching the element pattern. The elements may have electrodes formed prior to stacking or may have electrodes due to the stacking with the modules 28.

One or more modules 28 are positioned against the array 32. Each module 28 includes a frame 30, one or more circuits 34, flexible circuit material 36, and backing 38. Additional, different, or fewer components may be provided. For example, a printed circuit board or cable connector 48 is provided on each module 28. As another example shown in FIGS. 3 and 4, wire bonds are used instead of flexible circuit material 36

The frames 30 are metal, such as copper or aluminum. Plastic, fiberglass, cured epoxy, polymer, or other material may alternatively or additionally be provided. The frames have a generally plate-like shape, such as being square or rectangular with a thickness (shown left to right in FIG. 1) less the 50% of the width (into the page as shown in FIG. 1) or length (height as shown in FIG. 1). The notches or recesses 42 in both sides are deep enough to house and protect the circuit 34. A larger pitch array may use a thicker cross section frame.

The metal structure extends from adjacent the circuit 34 to a location further away from array. In one embodiment, the metal structure extends from adjacent the array 32 to a location spaced further from the array 32 than the circuits 34. There may be intervening structures for "adjacent," such as the flexible circuit material 36 and/or backing 38. Adjacent may be immediately adjacent or abutting or may be relative (e.g., the closest part of a component or adjacent as opposed to the housing).

The metal structure is positioned to passively conduct heat generated by the array 32 and/or the circuit 34 away and to a location spaced further away from the array 32. The metal structure may have a width (e.g., distance in elevation or azimuth across the array 32) greater than or less than the width of the array 32 and/or circuit 34. The length or distance from the array 32 in range is greater than the length of the circuit 34, but may be less. Any thickness may be used. The metal structure is a flat sheet, but may have bends or other shapes. Other portions of the frame 30 may extend to different extents in any direction or the frame may be all metal. In one embodiment, the frame 30 has a T-shaped cross section.

Figure 2:
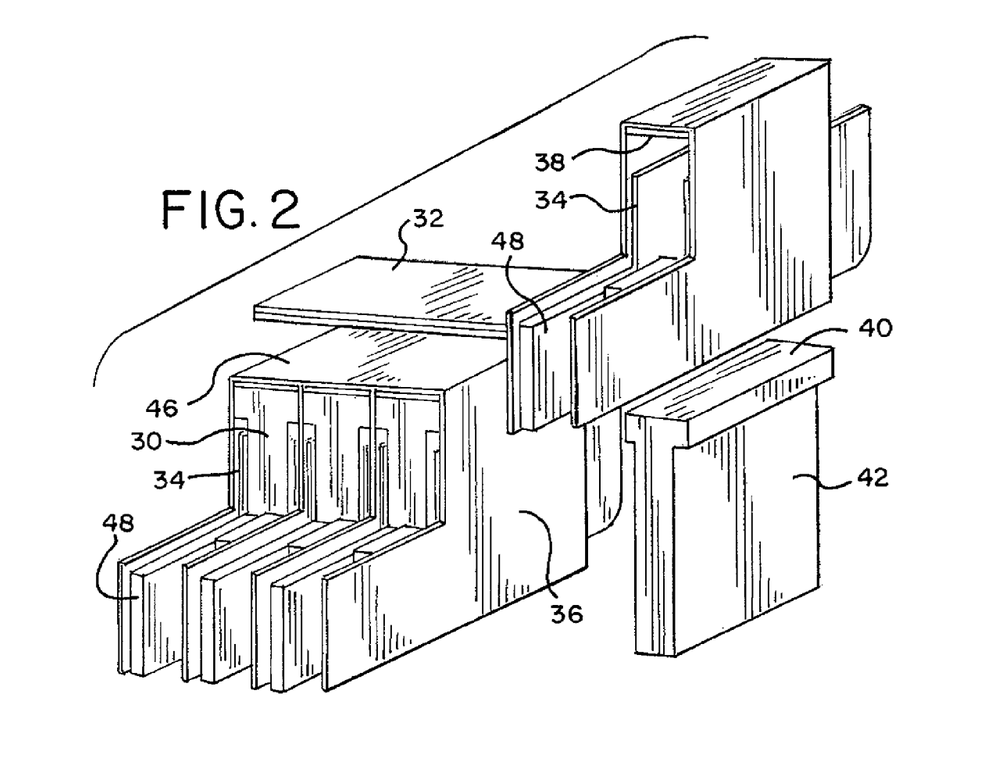
FIG. 2 is a perspective view of a plurality of transducer modules in another embodiment with an exploded view of one of the modules.

In one embodiment shown in FIGS. 1 and 2, the frames 30 are metal plates with a support portion 40 and a recess 42. The support portion 40 is a block, tube, or other shape for supporting a portion of the array 32 by forming the surface 44. The support portion 40 has a thickness corresponding to a given number of rows of the ultrasound transducer elements. The thickness is sized based on the pitch of the elements and the number of rows or columns to be supported. For example, 3-10 elevation spaced rows or elements are supported and the thickness is the same as the rows of elements in elevation. In one embodiment, twelve element rows are used for each frame 30. The number of rows depends on the number of elements and/or rows with which the integrated circuit or circuits 34 connect and operate. One, two or more integrated circuits 34 connect with a given frame 30 and the frame 30 is sized in thickness to support the resulting number of elements. Greater or fewer numbers of rows may be supported.

The width of the support portion 40 of the frame 30 is the same as or longer than the width of the array 32. For example, the width of the frame 30 is as long as or longer than the distance in azimuth of the array 32. To limit the size of the probe, the width of the frame 30 is the same or only 1-10% longer than the array 32.

In other embodiments, the frame 30 covers only a fraction of the width of the array 32, such as just ½ or ⅓. Multiple frames 30 may be stacked together along the azimuth or width dimension to support the array 32. Alternatively, the support portion 40 supports only a portion of the array 32 and other structure supports the rest of the array 32.

The width of the frame 30 may vary as a function of depth or length. Portions spaced away from the array 32 may have greater or lesser width. For example, the support portion 40 is a width of the array 32, but the frame 30 at the recess 42 is tapered inward (less width) to provide a smaller probe or tapered outward due to more room being available away from the array 32. In other embodiments, tapering of the frame 30 is not used except to form a curved array surface.

The support portion 40 extends from the array 32 and the surface 46 formed by the support portion 40. The portion of the frame 30 with the recess 42 continues the extension of the frame 30 from the support portion 40 and away from the array 32. The entire portion by the recess 42 extends to the location further from the array 32 than the circuit 34. Alternatively, only a part, such as the outside edges, extends the full distance.

The frames 30 are substantially perpendicular to the array 32 and the surface formed by the support portions 40. "Substantially" accounts for curved arrays 32 (see FIG. 7), or frames angling by 10 degree draft per side or less away from normal to the array 32.

The recess 42 is sized for connecting with the circuit 34, such as a chip of an integrated circuit. The recess may be an indention, hole, or other enclosing shape in the frame 30 for accepting the circuit 34. The recess 42 is a shape and dimensions the same or slightly larger than the circuit 34 (i.e., semiconductor chip). The recess 42 is sized for insertion of the circuit 34. In the embodiment of FIGS. 1 and 2, the recess 42 is a thinner or narrower region of the frame 30 such that the circuit 34 is not enclosed, but is positioned to allow stacking of the modules 28. The recess 42 is as deep or deeper than the integrated circuit 34 is thick, allowing the support portions 40 of adjacent modules to abut each other. The same thickness is provided across the entire portion of the frame 30 by the recess 42, but the thickness may be different at different locations. Other relative positions and orientations than shown may be used.

FIG. 1 shows two recesses 42, one on each side of the frame 30. The frames 30 of FIGS. 1 and 2 support two integrated circuits 34. In other embodiments, only one recess 42 is provided for only one circuit 34 per frame. Alternatively, more than one circuit 34 may fit in a given recess 42 and/or three or more recesses 42 may be provided, such as having slots in the frame 30 for the circuits 34.

Figure 3:
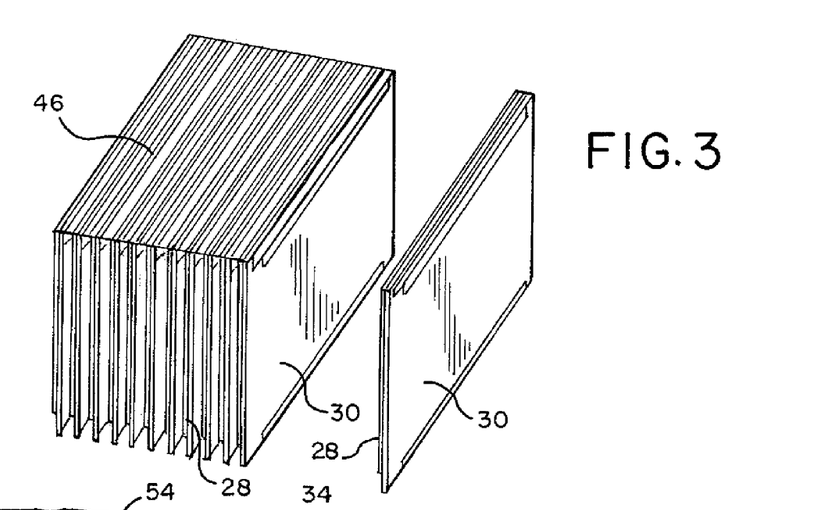
FIG. 3 is a perspective view of another embodiment of a stack of modules.
Figure 4:
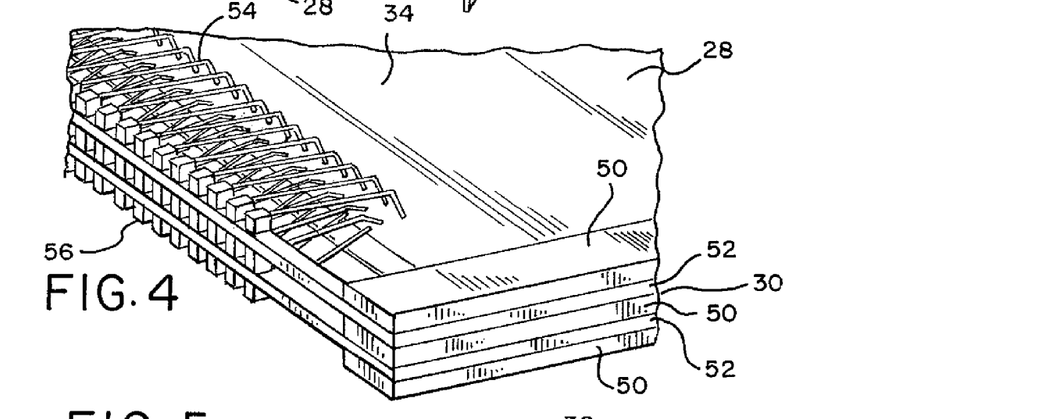
FIG. 4 is a perspective view of a portion of one of the modules of FIG. 3.

FIGS. 3 and 4 show an alternative embodiment of the frames 30. The frames 30 have similar dimensions as the frames 30 of FIGS. 1 and 2, but may be narrower. The recess 42 is an indentation to hold one circuit 34, but may have indentations on opposite sides to hold two circuits 34.

The frames 30 are formed from a composite of a plurality of layers of metal 50 and electrical insulator material 52. Three metal layers 50 and two insulator layers 52 are shown, but other numbers may be provided. The metal and insulator layers 50 and 52 are the same or different in size and shape. For example, the middle metal layer 50 or a bottom metal layer 50 is a sheet of metal for thermal conduction. The other layers are frames for forming the recess 42 or recesses 42. As another example, all of the layers 50, 52 are frames forming a hole as the recess 42.

In one embodiment, the number of metal layers 50 matches a number of rows to be supported by the frame 30 and electrically connected to the circuit or circuits 34 for the frame 30. Each metal layer 50 includes element backers 56. The element backers 56 are cubes, plates, electrodes or other structure for electrically connecting with elements of the array 32. The element backers 56 are formed by etching (e.g., acid etching), depositing, cutting, thinning, or other processes from the metal (e.g., copper) of the metal layer 50. For example, the element backers 56 are separated from each other within a metal layer 50 by dicing. The element backers 56 are separated from the rest of the metal layer 50 by etching or dicing after being stacked with the other layers 50, 52 to hold the element backers 56 in place. Other processes may be used.

The insulation layers 52 separate the metal layers 50 to provide the desired element pitch for the element backers 56 along one dimension. The insulation layers 52 also electrically separate the metal layers 50 from each other. The element backers 56 are held in place by the insulation layers 52.

Cured epoxy, polymer, or other material may be used for electrical insulation layers 52. Alternatively, the insulation layers 52 are themselves a composite of different materials.

The circuits 34 are semiconductor chips, analog components, digital components, processors, field programmable gate arrays, memories, combinations thereof, or other components. In one embodiment, the circuits 34 are integrated circuits, such as application specific integrated circuits manufactured as one or more chips.

The circuits 34 of different frames are of the same type. The same design of circuit 34 is repeated for each frame 30. For example, a given application specific integrated circuit is the same as another application specific integrated circuit. Two parts are provided, but the two parts are of the same design. The same application specific circuits may be used for each frame 30. More than one type may be used, such as one type of circuit 34 for one recess 42 and another type of circuit 34 for another recess 42. The circuit design may be used in any of various arrays, such as providing beamforming or multiplexing the same for any connected sub-apertures. Alternatively, different designs are used for different probes.

The circuit 34 reduces the number of channels of information to be communicated to an imaging system. Any reduction technique may be used. For example, the semiconductor multiplexes using time and/or frequency multiplexing. As another example, the semiconductor includes pulsers, such as switches, for generating waveforms, limiting the number of cables for transmit waveforms. Transmit and/or receive beamforming components may be included, such as delays, phase rotators, amplifiers, summers, or other components for relatively delaying and apodizing transmit and receive apertures. For receive beamforming, summation may be used to partially beamform for a sub-aperture of the array of elements. In other examples, the circuit 34 includes a mixer, or switches with an amplifier for mixing signals from different elements onto fewer channels. The semiconductor may include circuitry other than for channel reduction, such as analog-to-digital converters, controllers, transmit/receive switching, and/or filtering.

The circuit 34 includes the entire or any portion of the beamformer, mixer or other component. The circuit 34 may filter, process, or condition signals without channel reduction. The circuit 34 may include clock, control, and signal routing.

Another circuit or device, such as on the interface board 48, may reduce the number of channels.

The circuit 34 receives signals from the elements of the array 32. The circuit 34 outputs data after processing the signals. The output data is analog or digital. The output data is provided to the interconnect board 48.

One or more circuits 34 connect with each frame 30, such as the frames 30 of FIG. 1 holding two circuits 34 in two recesses 42. The metal plate or other structure of the frame 30 provides a surface to which the circuits 34 may be connected. The circuits 34 connect with the frames 30 by bonding. Thermal epoxy, thermal tape, or other material bonds the circuits 34 to the frames 30. The circuits 34 connect to the frames 30 in the recesses 42.

Due to the orientation of the frames 30, the recesses 42 and connected circuits 34 are substantially perpendicular to the array 32. For example, multiple ASICs are perpendicular to array, increasing the usable ASIC area. In the embodiment of FIG. 1, a 10 mm×10 mm array area may be connected to a plurality of ASICs, each with an 8×12×6 mm ASIC area. The substantially perpendicular positioning increases the spaced available for the circuits 34.

After connection, the frame 30 includes a portion, such as a thermally conductive portion, extending away from the heat generating components. For example, metal structure extends further away from the multi-dimensional array than the circuits 34 after bonding. The location of greater extent may be along the range dimension or may be at an angle away from normal to the array. The frames 30 provide a mechanical structure and a thermal conduction path to remove heat from the electronics.

The recesses 42 in the frames 30 position the circuits 34 near the array 32. The circuits 34 are connected with the elements of the array 32 for transmit and/or receive operation. Conductors electrically connect the circuits 34 to the array 32. For FIGS. 1 and 2, the conductors are traces on the flexible circuit material 36. FIGS. 3 and 4 show the conductors as the wire bonds 54. The conductors may include different portions, such as traces soldered to or connected with pads, wires, electrodes, wire bonds, or other conductor. The conductors may include portions for exposure on a surface for contact with elements and portions for contacting input/output pads of the circuit 34.

The conductors connect the elements or corresponding electrodes to the circuit 34 (e.g., connect to inputs of the integrated circuit). The conductors extend from the circuit 34 to the elements. The conductors are short, such as having no, one or two right angle turns without folding or having just one or two bends of equal angles or bends each of less than 90 degrees.

In the embodiment of FIGS. 1 and 2, traces are formed or deposited on the flexible circuit material 36. The flexible circuit material 36 is Kapton® or other electrically insulating material. The flexible circuit material 36 may or may not have active and/or passive circuit components. For example, the flexible circuit material 36 has only traces and pads for electrically connecting the circuit 34 to the array 32. In one embodiment, discrete capacitors are used on the material 36 along with the circuits 34. The capacitors store energy required for circuit operation. Resistors and some small integrated circuits on the material 36 may support the primary circuit function. For example, discrete voltage regulators are on the flex circuit material 36 for the main power supply.

Any number of flexible circuit material components may be provided. For example, a single sheet, strip or other shape of flexible circuit material 36 is provided for a given frame 30. The flexible circuit material 36 is cut or formed in a desired shape. As shown in FIG. 1, the flexible circuit material 36 covers the recess 42 and/or circuit 34 and wraps at least partially around sides of the frame 30 at the recess portion. The flexible circuit material 36 goes from one side of the frame 30, over a top of the frame, and down to the other side. At least a portion of the flexible circuit material 36 connects with and extends from the circuit 34 on one side or circuits 34 on two sides to between the multi-dimensional array 32 and the frame 30. In another embodiment, the flexible circuit material 36, as one or two separate sheets, extends only from the top of the circuit 34 to the elements of the array 32. Any number of flexible circuit material components may be provided for each circuit 34, such as one flexible circuit material strip for each frame (e.g., two circuits 34). One, two, four, eight or other numbers of circuits 34 are provided for a given flexible circuit material 36.

The support portion 40 of the frame 30 is flat, curved, or forms another surface. The flexible circuit material 36 rests flat and/or tightly on top of the support portion 40 underneath the array 32. A single layer of flexible circuit material 36 is between the array 32 and the frame 30. The single layer may be double- or single-sided flexible circuit material 36. Multilayered material 36 may be used, such as two, three or other number of laid-out flat layers with or without folds under the footprint of the array 32. The traces terminate at pads or end for connection with the elements of the array 32. The traces are coated or covered to insulate them from the frame 30 and/or the array 32. For example, an insulation layer, such as the backing 38 or a coating, electrically insulates the traces from the frame 30. Vias through the flexible circuit material 38 connect the traces with the elements 32, such as a two or multilayer flex using vias to connect circuits 34 on one side to elements on another side. A bonded, non-bonded (i.e., contact), or other connection may be used. By having the flexible circuit material 38 over the support portion 40 of the frame 30, the traces are positioned to contact the elements.

The traces on the flexible circuit material 38 allow differences in the connection arrangements between the circuit 34 and the elements of the array 32. For example, the pitch of the pads on the circuit 34 is in any arrangement. The pads are for input, output, or both. The traces electrically connect with the pads. The traces are routed to the different pitch of the elements. Different pitches in one or two dimensions are provided for the elements than for the circuit 34. Where different arrays are used for different probes, the same circuit 34 may be used by changing the trace layout of the flexible circuit material 38. The flexible circuit material 36 connects the circuit (e.g., ASIC) pitch to the acoustic stack pitch.

Since different arrays 32 and/or circuits 34 may have different connection configurations or pitch, the traces are patterned to match the differences. For example, the pitch of inputs of the circuit 34 is smaller along two dimensions of the pad surface than the pitch of the elements, so the traces fan apart in two-dimensions. Other redistribution may be used. The pitch for the circuit 34 may be one-dimensional along an edge of the chip, may be two-dimensional by being along a plurality of edges of the chip, or may be two-dimensional on one or more surfaces of the chip. The redistribution allows use of module circuits 34 with different arrays 32. Since different patterns of the traces may be used, the same circuit 34 may be used with different element pitches. Different circuits 34 may be used with the same element pitch.

In the embodiments of FIGS. 3 and 4, wire bonds 54 connect the element backers 56 to the circuit 34. The wire bonds 54 are gold, copper, or other conductors. The element backers 56 are at a pitch of the elements of the array 32. The wire bonds 54 are arranged to provide electrical isolation while connecting from the input/output pads of the circuit 34 to the element backers 56. The pitch of the element backers 56 is the same or different than the pitch of the pads of the circuit 34. The difference is along one or two dimensions. The wire bonds 54 for a given frame 30 connect to the element backers 56 of one or more rows of elements. In one embodiment of FIGS. 3 and 4, a multi-layer lead frame is provided with leads arranged at the array pitch in both dimensions. The lead frame contains the circuit 34 and may be provided as a pre-tested assembly. Wire bonds from the circuit 34 to the lead frame fan out or in in two dimensions to adapt to the lead frame pitch. The entire lead-frame+wire-bonds+circuit 34 assembly is covered with mould compound or other protective covering.

For the embodiments of FIGS. 1-4, the frames 30 are sized to stack along the elevation and/or azimuth extent of the array 32. Any number of frames 30 is stacked to support the array 32. For example, 12-16 frame assemblies of FIGS. 3 and 4 support one multi-dimensional array 32. As another example, each frame assembly of FIGS. 1-2 connects with three rows of forty eight elements. The shape of the modules 28 provides for the stack to be parallel or non-parallel, such as forming a flat surface for a linear array or forming a curved surface for a curved array.

In stacking the modules 28, the modules 28 are bonded together. An encapsulation compound bonds the modules 28 together. The encapsulation compound covers and electrically insulates the circuit 34 as well. The wire bonds 54 and/or flex circuit material 36 are held in place by the encapsulation compound.

The stacked modules 28 are stacked adjacent to the multi-dimensional array 32. Fiducials, a frame, or other structure aligns the frames 30 with the array 32. For stacking, the frames 30 and respective circuits 34 are aligned with the elements of the array 32. The element backers 56 or traces are positioned to line up with the elements.

The stack of modules 28 is formed or bound together and then stacked against the array 32 for bonding to the array 32. Alternatively, the modules 28 are stacked together and adjacent to the array 32 and all bonded together. The insulation coating, epoxy, or backing material insulates conductors of each frame 30 from other frames 30.

The stack of frames 30 provides a surface 46 of exposed element contacts, such as vias, pads, or traces on the flexible circuit material 36 or the element backers 56. Alternatively, the stack of frames 30 is ground to expose the element contacts. Etching may be used to recess the surrounding material to better expose the element contacts on the surface 46. The element contacts are electrically isolated from each other by bonding and/or insulation material. The element contacts are distributed on the surface 46 in correspondence with the element distribution of the transducer. Each element contact may be used as an electrode of the array 32 or for connecting with the element electrodes. A sufficient number of frames 30 are provided for the number of elements.

The stacked frames 30 and/or array 32 are laminated together. Heat or other activator may be used for lamination. Epoxy or other binding agent may be used. In an alternative embodiment, a rigid structure or clamp holds the stack together during use.

The support portions 40 of the frames 30 form the surface 46. The surface 46 is positioned adjacent to the array 32. One or more intervening layers from the frames 30 may be provided, such as the flexible circuit material 36 and/or the backing 38. The surface 46, due to the shape of the frames 30 or after bonding, is shaped to support the array 32, such as being flat or curved in one or two-dimensions. The surface 46 is sized and shaped to support the array 32.

Figure 5:
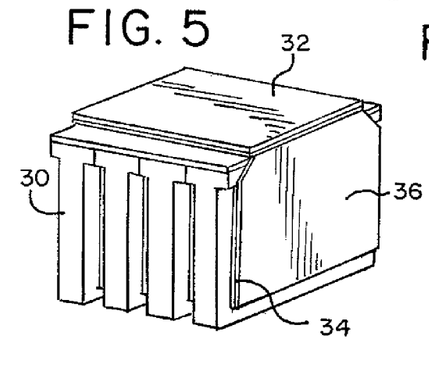
FIGS. 5-7 are perspective views of three example embodiments of transducer probes with modules.
Figure 6:
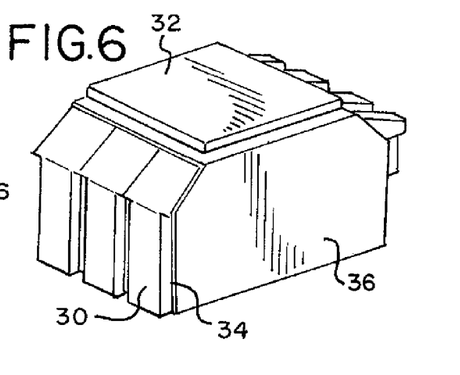

FIGS. 1-2 show a stack of four frames 30 for use with eight circuits 34 and an array 32 of any pitch in azimuth and/or elevation. Other combinations may be used. For example, 448 elements and associated channels connect with 14 ASICs on 7 frames 30. The flexible circuit material 36 fans traces in from an ASIC pitch (e.g., 0.250 mm) to an acoustic stack pitch (e.g., element pitch of 0.220 mm along both dimensions). As another example, 192 elements and associated channels connect with 6 ASICs on 3 frames 30. The flexible circuit material 36 fans traces out from the ASIC pitch to the acoustic stack pitch (e.g., 0.400 mm). FIG. 5 shows another example. 256 elements and associated channels connect with 8 ASICs on 4 frames 30. The flexible circuit material 36 fans traces in from the ASIC pitch to the acoustic stack pitch (e.g., 0.200 mm) FIG. 6 shows another example. 192 elements and associated channels connect with 6 ASICs on 3 frames 30. The support portion 40 of the frames tapers inward from the surface 46, but may not taper or may taper outward. The flexible circuit material 36 fans traces in from the ASIC pitch to the acoustic stack pitch (e.g., 0.175 mm). In yet another example, 768 elements and associated channels connect with 24 ASICs on 6 long frames or 12 short frames (e.g., 2 frames stacked along one dimension and 6 along another). The flexible circuit material 36 fans traces out from the ASIC pitch to the acoustic stack pitch (e.g., 0.300 mm). Other arrangements are possible.

Figure 7:
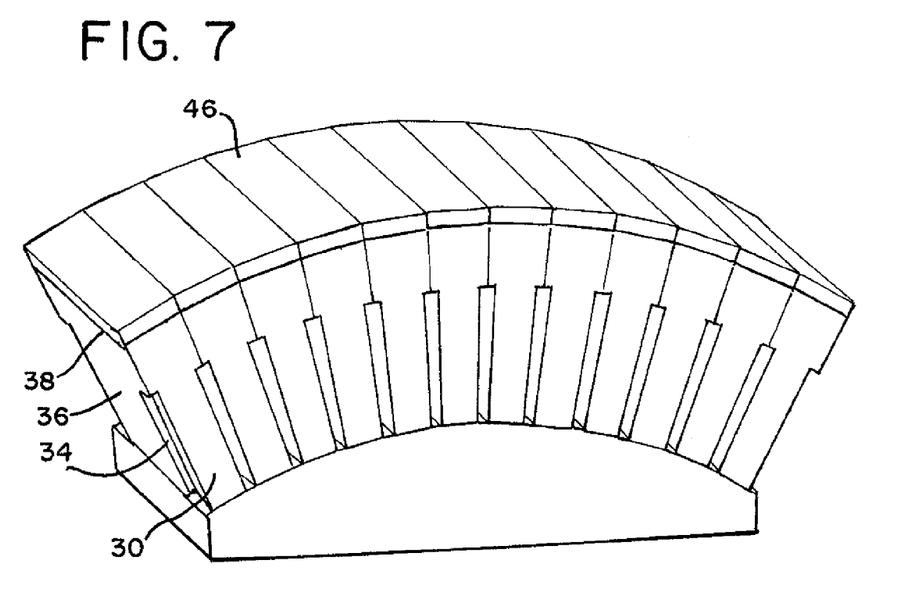

In the examples of FIGS. 5 and 6, the frames 30 stack together squarely along a single dimension. The sides of the support portions 40 and/or other portions of the frames are flat and square. The thickness of the portions of the frames 30 abutting each other is the same. FIG. 7 shows an alternative embodiment. The thickness of the frames 30 varies. The frames 30 taper, such as being thicker at the top or surface 46 and thinner spaced away from the surface 46. The taper results in a generally curved surface 46. Concave or convex curvature may be provided. Two dimensional curvature may be provided. The support surface of each frame 30 is flat or curved. Either complete or walking apertures may be supported using an array on the generally curved surface 46. Generally accounts for flat frames 30 at different angles to step through the curve.

The backing 38 is flat and thin. Alternatively, the backing 38 is shaped to further form the surface 46, such as being formed or stacked on top of a flat top of the frame 30, but providing some curvature for supporting the flexible circuit material 36 and the array 32. The backing 38 is formed separately over each frame 30 by depositing, by pouring and curing, or by molding and stacking. In one embodiment, the backing is held in place by encapsulating the circuit 34, by other bonding, or by the flexible circuit material 36.

The backing 38 is acoustically attenuating material, but may alternatively or additionally match the ultrasound frequency in order to deflect acoustic waves away from the array 32. In one embodiment, the backing is molded loaded epoxy, such as tungsten-loaded epoxy. Other backing materials, including solids, polymers, semi-solids, or epoxies, may be used. No or different loading materials may be used. The density of the loading material or base backing material may vary, such as altering the acoustic attenuation from one side of the backing 38 to another side.

A portion of the frames 30 may connect with a heat sink. To more efficiently draw away or remove heat, the heat sink connects with the frames 30. The bottom surface, bottom portion, or other portion of each frame 30 connects with separate or the same heat sink. In one embodiment, the heat sink connects with locations on the frames 30 spaced further from the array 32 than the furthest most portion of the circuit

34. Passive cooling is provided within each frame 30. The metal structure or other thermally conductive material passes heat by contact to the heat sink.

The heat sink uses active and/or passive cooling. For example, the heat sink includes a plurality of fins for radiating or exchanging heat with air passing through vents. A fan may force air over the fins. In another example, a pump and heat transfer system use fluid or gas to move heat transferred from the frames 30 away from the frames 30.

In other embodiments, the frames 30 include channels, grooves or other tube structures for coolant. Forced gas or fluid passes through the tubes for active cooling. A pump moves the fluid through the tubes. The tubes may or may not be lined. Fins or other structure for drawing heat out of the fluid is spaced away from the frames 30, array 32, circuits 34, and/or probe.

In other embodiments, the frames 30 may be attached to a heat pump such as a thermal electrical cooler or heat pipe. This heat pump cools the array/patient contact surface while moving the heat to a less sensitive area.

The heat sink, whether active or passive, is positioned next to the frames 30. The heat sink may be on the cable interface boards 48. Alternatively, the cable interface boards 48 extend from a side of the frames 30 and the heat sink connects with a bottom or other side of the frames 30. In other embodiments, the heat sink is spaced from the frames 30, such as being in another portion of a handheld probe or even being positioned outside of the probe (e.g., in an imaging system).

The cable interface boards 48 are interconnect boards. In one embodiment, the cable interface boards 48 are printed circuit boards of insulating material with signal traces, vias, and a coaxial cable connector. Active or passive circuits may or may not be provided on the cable interface boards 48. For example, capacitors are provided for power storage or DC decoupling.

A separate cable interface board 48 is provided for each of the frames 30 as shown in FIGS. 1 and 2. Alternatively, the circuits 34 of more than one frame 30 connect with a given cable interface board 48. More than one cable interface board 48 may be used for a given frame 30, such as a separate cable interface board 48 for each circuit 34.

The cable interface boards 48 are bonded, clamped, or otherwise connected to the frames 30. Alternatively, the cable interface boards 48 are stacked adjacent to the frames 30 without being connected directly or fixedly to the frames 30. The cable interface boards 48 are positioned below or beside the frames 30. The cable interface boards 48 are connected to each frame 30 and then stacked or are stacked separately from the frames 30 and then positioned against the frame stack.

Wire bonds, flexible circuit material traces, or other conductors electrically connect pads or wires of the circuits with the cable interface boards 48. In other embodiments, flip chip type soldering connects the boards 48 with the circuit 34. The recess 42 has sufficient depth to allow for both the circuit 34 and the boards 48. In other embodiments, the flexible circuit material 36 includes separate traces for connecting the circuits 34 with the boards 48.

The cable interface boards 48 connect the outputs of the circuits 34 to cables, such as coaxial cables. Control signals, power, and/or transmit waveforms may be provided through or by the cable interface boards 48 to the circuits 34 using one or more conductors. The cable interface boards 48 may provide signals from the elements connected with one or more circuits 34. The cable interface boards 48 may interconnect circuits 34 on the same frame 30. The cable interface boards 48 may interconnect between frames 30 so that signals from one circuit 34 on one frame 30 may be provided to another circuit 34 on another frame 30.

In alternative embodiments, the cable interface boards 48 interface with other types of cables or perform wireless interfacing. For example, full beamformation for transmit and receive operation are performed in the probe (e.g., by the circuits 34 and/or circuits of the boards 48). The resulting digital samples may be transmitted using any data transmission technique or standard.

Figure 8:
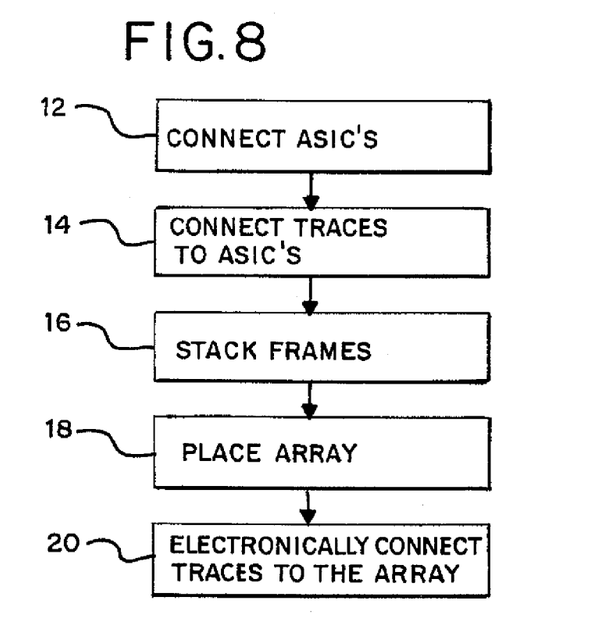
FIG. 8 is a flow chart diagram of one embodiment of a method for stacking modules for assembling a transducer probe.

FIG. 8 shows one embodiment of a method for stacking an ultrasound probe. The components are stacked to form an ultrasound transducer. The stack is for operation with a multi-dimensional transducer array, but may operate with a one-dimensional array.

The method is performed in the order shown. Alternatively, a different order is provided. For example, the traces are connected to the application specific integrated circuits (ASICs) in act 14 prior to connecting the ASICs to the frames in act 12. Additional, different, or fewer acts may be provided. For example, each frame is formed by stacking metal structure and insulation material prior to performing act 12.

In act 12, one or more ASICs are connected to a frame. Each of a plurality of frames has ASICs connected. The ASICs are placed in and/or against the frames. Insulation material on the frame or on the ASICs avoids undesired electrical contact. Alternatively, the flexible circuit material is positioned between the ASICs and the frames. In other embodiments, the substrate side of the ASICs without any exposed electrical contacts is positioned against the frames.

The ASICs connect to the frames by bonding, such as with epoxy. Alternatively, clamping or a temporary connection is used (e.g., wax).

In act 14, traces on flexible circuit material are connected to the circuits. One or more sheets of material with traces are positioned against the ASICs. Flip-chip soldering, low temperature silver epoxy cure, or other process is used to connect the traces to the exposed wires, pads, or other inputs or outputs of the ASICs. The material is placed over the frames and ASICs and connected to the one or more ASICs. Alternatively, the material is connected to one ASIC, pulled over the frame, and then connected to another ASIC. For example, the chips are reflowed onto the flex substrate first. Then, the flex substrate is bonded to the frame. The sides are then bent over. The backing may be formed on or positioned on the frame prior to connection of the material.

The connections for the cable interface boards or other components may be made with each frame separately. The connections are electrical and/or physical. The connections may encapsulate or otherwise electrically isolate or cover components.

In act 16, the frames are stacked adjacent to each other. Two or more frames are aligned. The alignment positions the frames to form the surface. The frames are stacked immediately adjacent to each other or with intervening components, such as an electrical insulation sheet or plate between them.

The frames are stacked to provide the surface for the array with exposed conductors for connecting to the elements of the array. The stacking may cover the conductors, but the conductors may then be exposed by lapping or cutting.

As stacked, the frames and ASICs are substantially perpendicular to the surface for supporting the array. The frames include metal or other thermally conductive material extending from adjacent to the surface and/or the ASICs to a location spaced away from the surface. The location is spaced further from the surface than the ASICs, but the frame may extend less than the ASICs away from the surface.

In act 18, the multi-dimensional transducer array is placed on the stack of frames. Fiducials, a frame, or other structure aligns the array to the exposed contacts of the frame stack. The stack of frames may be etched, ground, or cut to expose the contacts. The array is diced prior to stacking. Alternatively, the array is diced after placement where the dicing separates the contacts in the stack for electrical isolation.

The array includes elements with or without electrodes. For example, the contacts of the stack provide the electrode on one side of the array and a grounding plane above the array provides the other electrode for each element. The array may include one or more matching layers.

After positioning the array on the stack, the array is bonded to the stack. The bonding is with epoxy or other agent. The bonding is performed separately from other bonding acts or is part of bonding the frames together, the ASICs to the frame, encapsulating the ASICs, or other bonding.

With the array on the surface formed by the frames, the ASICs are substantially perpendicular to the multi-dimensional transducer array. The array is positioned as a single layer (e.g., one component with or without a multi-layer structure) on the stack of frames. The array may be placed, and then other layers placed on the array. Other layers may be positioned between the array and the surface.

In another embodiment, an individual frame 30 may have a respective array fabricated on the frame before attaching additional frame assemblies with respective pre-fabricated arrays. FIG. 7 shows one example of this approach.

In act 20, the traces are electrically connected to the multi-dimensional transducer array. The electrical connection is provided by contact. Alternatively, soldering, such as bump soldiering or silver epoxy, is provided.

The placement of the array on the stack of frames aligns the contacts of the frames with the elements of the array. A two-dimensional pitch of the traces matches the pitch and positioning of the elements. The traces connect to the circuits in a different two-dimensional pitch of the traces. The surface of the stack of frames supports the layer of flexible circuit material. The contacts are provided on the flexible circuit material over the surface. By placing the array on the flexible circuit material, electrical connection is made between the elements and the circuits.

A redistribution layer between the acoustic elements and the flexible substrate may route the metal traces from the electronics. The redistribution layer may be useful for holding the precut acoustic stack, along with simplifying the alignment requirements between the acoustic stack and flexible substrate.

The cable interface boards and/or heat sink may be attached. For example, the heat sink is connected to the stack of frames using thermal epoxy.

In another embodiment, the frames 30 are electrically independent except for grounding. No electrical connection between the circuits 34 of different frames is provided other than local ground. In this design, the frames 30 stand on their own and do not require any connections between frames 30 in the probe tip. Frame-to-frame electrical interconnection may be difficult.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ultrasound transducer probe comprising:
a multi-dimensional array of ultrasound transducer elements;
a plurality of frames stacked adjacent to the multi-dimensional array, each of the frames comprising metal structure extending from adjacent to the multi-dimensional array to a location spaced away from the multi-dimensional array and each of the frames supporting multiple of the ultrasound transducer elements of the multi-dimensional array; and
a plurality of circuits connected with the transducer elements, the plurality of circuits connected with respective frames, the location being further away from the multi-dimensional array than the location is from the circuits wherein each of the frames comprises a support portion positioned adjacent to the multi-dimensional array, the support portion having a thickness corresponding to a number of rows of the ultrasound transducer elements connected with the circuit or circuits connected with the frame, and wherein each of the frames comprises a circuit portion narrower than the thickness, the circuit or circuits connected with the circuit portion such that the support portions of adjacent frames substantially abut each other.

2. An ultrasound transducer probe comprising:
a multi-dimensional array of ultrasound transducer elements;
a plurality of frames stacked adjacent to the multi-dimensional array, each of the frames comprising metal structure extending from adjacent to the multi-dimensional array to a location spaced away from the multi-dimensional array; and
a plurality of circuits connected with the transducer elements, the plurality of circuits connected with respective frames, the location being further away from the multi-dimensional array than the location is from the circuits;
wherein the frames comprise metal plates having a recess in which one of the circuits is connected, the circuits being in the recesses perpendicular to the multi-dimensional array.

3. An ultrasound transducer probe comprising:
a multi-dimensional array of ultrasound transducer elements;
a plurality of frames stacked adjacent to the multi-dimensional array, each of the frames comprising metal structure extending from adjacent to the multi-dimensional array to a location spaced away from the multi-dimensional array; and
a plurality of circuits connected with the transducer elements, the plurality of circuits connected with respective frames, the location being further away from the multi-dimensional array than the location is from the circuits;
wherein the frames comprise a plurality of layers of metal and electrical insulator material and comprise metal element backers, wire bonds connecting the metal element backers to the circuit.

4. An ultrasound transducer probe comprising:
a multi-dimensional array of ultrasound transducer elements;
a plurality of frames stacked adjacent to the multi-dimensional array, each of the frames comprising metal structure extending from adjacent to the multi-dimensional array to a location spaced away from the multi-dimensional array and each of the frames supporting multiple of the ultrasound transducer elements of the multi-dimensional array; and a plurality of circuits connected with the transducer elements, the plurality of circuits connected with respective frames, the location being further away from the multi-dimensional array than the location is from the circuits and further comprising for each frame, flexible circuit material having traces connected with and extending from the circuit or circuits to between the multi-dimensional array and the frames, a portion of the flexible circuit material between the multi-dimensional array being a single layer and having contact pads connected with the traces for electrically connecting the circuit or circuits to the ultrasound transducer elements.

5. An ultrasound transducer probe comprising:
 a multi-dimensional array of ultrasound transducer elements;
 a plurality of frames stacked adjacent to the multi-dimensional array, each of the frames comprising metal structure extending from adjacent to the multi-dimensional array to a location spaced away from the multi-dimensional array and each of the frames supporting multiple of the ultrasound transducer elements of the multi-dimensional array; and
a plurality of circuits connected with the transducer elements, the plurality of circuits connected with respective frames, the location being further away from the multi-dimensional array than the location is from the circuits and further comprising for each frame, flexible circuit material having traces connected with and extending from the circuit or circuits to between the multi-dimensional array and the frames, a portion of the flexible circuit material between the multi-dimensional array being a single layer and having contact pads connected with the traces for electrically connecting the circuit or circuits to the ultrasound transducer element wherein the traces have a different pitch for connection with the circuit or circuits than for connection with the contact pads.

6. An ultrasound transducer probe comprising:
 a multi-dimensional array of ultrasound transducer elements, the ultrasound transducer elements distributed in azimuth and elevation;
 a plurality of frames positioned adjacent to each other such that a surface formed from the frames supports all of the multi-dimensional array, the frames each extending substantially perpendicularly from the multi-dimensional array and away from the surface;
 a plurality of circuits connected with respective frames such that the circuits are perpendicular to the multi-dimensional array; and
 flexible circuit material for each frame extending from the circuit or circuits and over the surface between the multi-dimensional array and the frames, traces of the flexible circuit material over the surface connecting with the ultrasound transducer elements.

7. The transducer probe of claim 6 wherein each of the frames comprises a metal structure with a support portion forming a respective portion of the surface, the support portion having a thickness corresponding to a number of rows of the ultrasound transducer elements connected with at least two circuits connected with the frame, and wherein each of the frames comprises a circuit portion narrower than the thickness, the at least two circuits connected with the circuit portion such that the support portions of adjacent frames substantially abut each other.

8. The transducer probe of claim 6 wherein the frames extend from the surface to a location spaced further from the surface than the circuits;
 further comprising a heat sink connected with the frames at the location.

9. The transducer probe of claim 6 wherein the flexible circuit material over the surface comprises a two or fewer layers with contact pads connected with the traces, the contact pads electrically connecting the circuit or circuits of each of the frames to the respective ultrasound transducer elements.

10. The transducer probe of claim 6 wherein the traces have a different pitch for connection with the circuit or circuits of each frame than for connection with the ultrasound transducer elements.

11. The transducer probe of claim 10 wherein the different pitch comprises a first two-dimensional pitch for the traces connected to the circuit or circuits and a second two-dimensional pitch different than the first two-dimensional pitch.

12. The transducer probe of claim 6 where circuits of each frame are electrically independent between the frames except for grounding.

\* \* \* \* \*